United States Patent [19]

Little et al.

[11] Patent Number: 4,738,175
[45] Date of Patent: Apr. 19, 1988

[54] DEFECT DETECTION SYSTEM

[75] Inventors: James A. Little, Gazelle, Calif.; Dennis Cavin, Medford, Oreg.

[73] Assignee: Simco-Ramic Corp., Medford, Oreg.

[21] Appl. No.: 813,121

[22] Filed: Dec. 24, 1985

[51] Int. Cl.$^4$ .......................... B26D 5/30; B26D 5/38
[52] U.S. Cl. .......................................... 83/71; 83/371; 83/519; 83/620; 83/289; 209/587
[58] Field of Search .................. 83/71, 371, 513, 519, 83/620, 639, 289; 234/107, 108, 109; 209/587

[56] References Cited

U.S. PATENT DOCUMENTS

| | | | |
|---|---|---|---|
| 3,664,397 | 5/1972 | Raye et al. | 83/371 X |
| 3,983,388 | 9/1976 | Gugliotta | 209/587 X |
| 4,114,488 | 9/1978 | Vornfett | 83/371 X |
| 4,186,836 | 2/1980 | Wassmer et al. | 209/587 X |
| 4,351,437 | 9/1982 | Long | 209/587 X |
| 4,493,420 | 1/1985 | Dennis | 209/587 |
| 4,520,702 | 6/1985 | Davis et al. | 83/371 X |
| 4,576,071 | 3/1986 | Rayment | 83/371 X |

Primary Examiner—E. R. Kazenske
Assistant Examiner—Scott A. Smith
Attorney, Agent, or Firm—Flehr, Hohbach, Test, Albritton & Herbert

[57] ABSTRACT

A defect detection system is especially applicable to string type potatoes for removing the black spots and includes removing or sorting out potatoes with black spots. It includes a pair of line scanning cameras focused on opposite sides of a vertical on a common line, spaced above the conveyor belt to the height of the potato. Such opposite sight lines provide for effective sensing of leading or trailing edges of the potato. To provide for effective cutting, the cutting blade units have offset blades to allow overlap and a spacing so that areas of uncertainty created by the two cameras are eliminated. To minimize down-time of the system, the vision light, power and punch modules are separately removable. Moreover, they are located on a cantilevered base above the moving belt. This cantilevering in conjunction with pivoted supports allows for a seamless belt and easy removal of that belt. Finally, off the shelf air piston drives are utilized, their rebound characteristics being optimized by the tailoring actuating pulses to match the specific rebound characteristics.

8 Claims, 11 Drawing Sheets

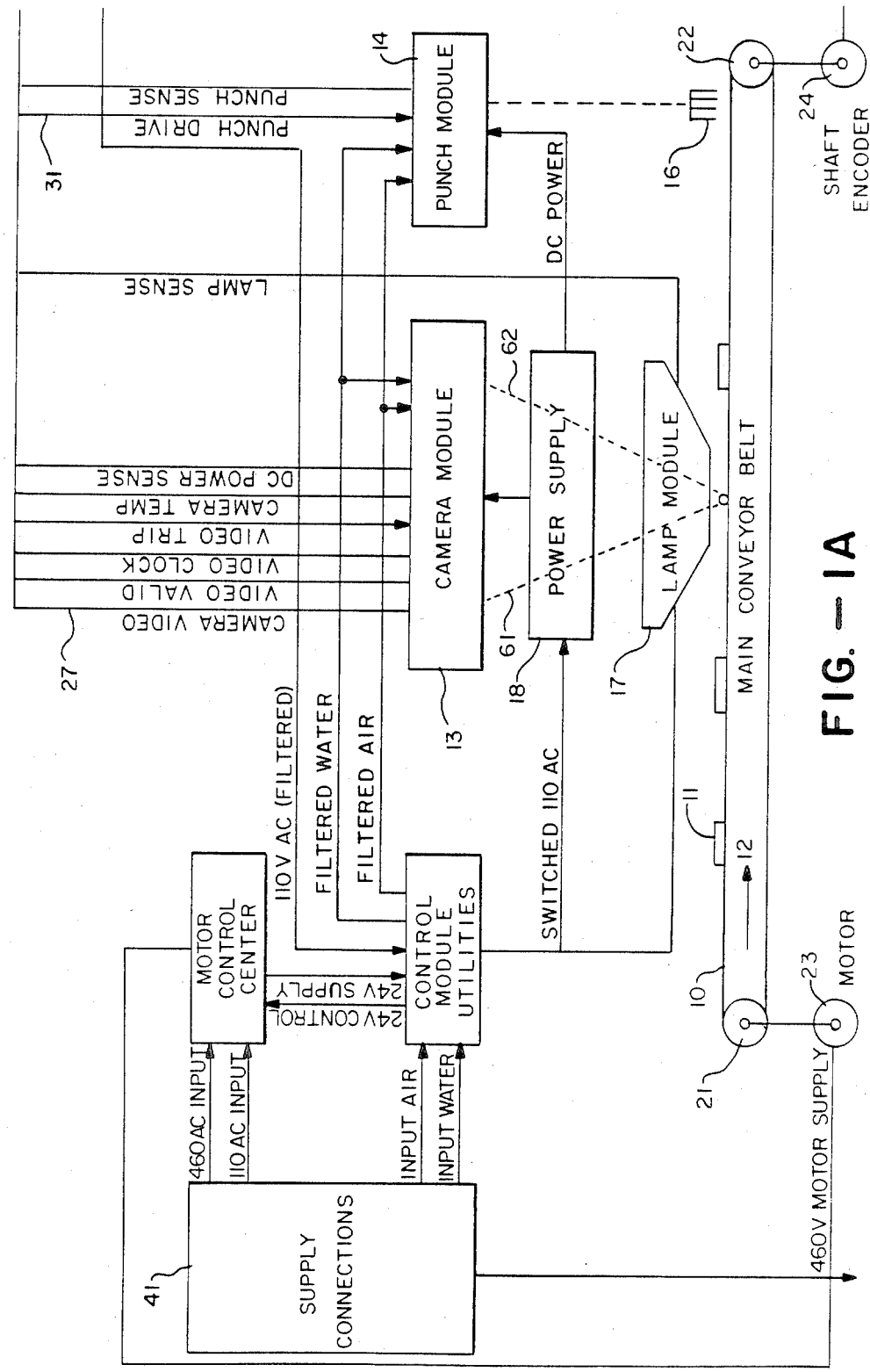
FIG.—1A

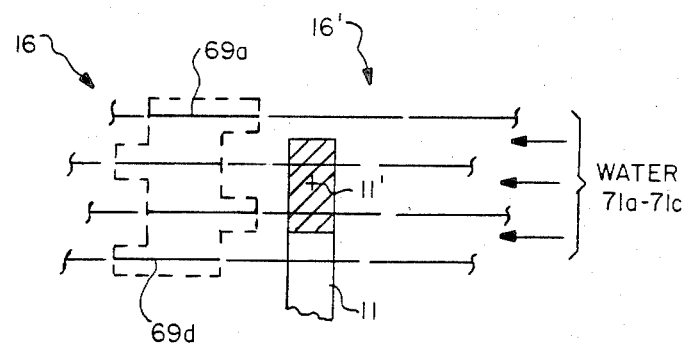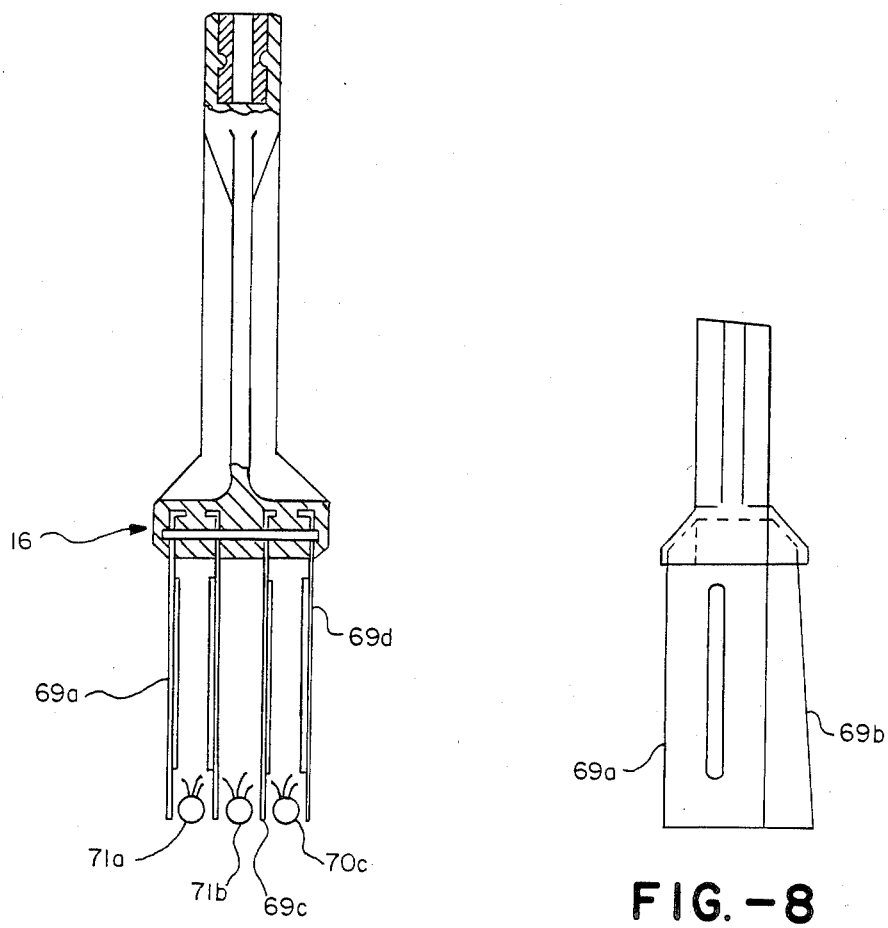

FIG.—11

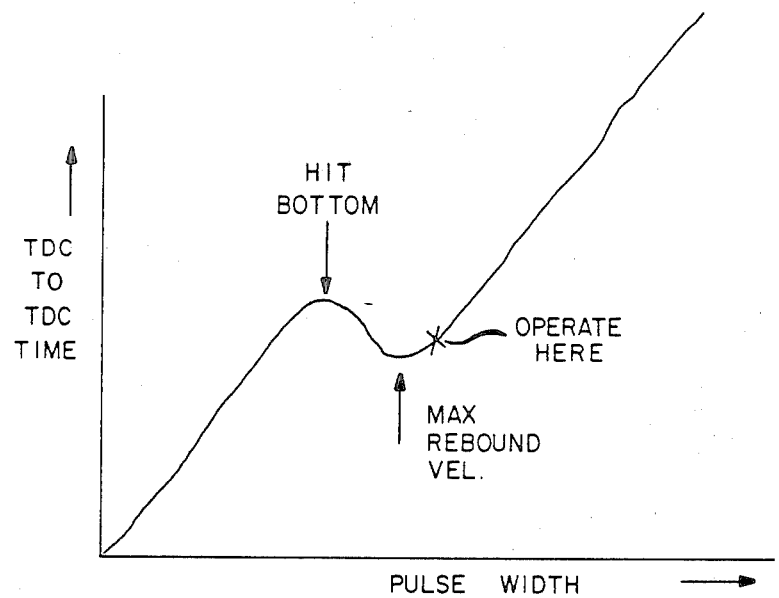
FIG.—13

DEFECT DETECTION SYSTEM

The present invention is directed to a defect detection system for sensing defects in discrete pieces of similar product being carried on a conveyor belt. More specifically, the product typically might be some type of food where a defect either based on size or color must be sensed and this defect removed; for example, the dark spots on French fried potato strips. Such removal may be done either by actually physically cutting the defect from the remainder of the food product or doing that on a sort operation.

The detection system of the above type must process thousands of pounds of raw food and other products. This must be done under ambient conditions which are sometimes adverse. Most importantly, the system must be reliable, in operation and easy to repair since any down time is very costly especially in the food processing industry. Furthermore, the automatic defect detection system must operate at a high efficiency to reliably sense defects or some color or size characteristic of a product to minimize later manual processing.

One part of the defect detection system in many applications is the use of a knife or blades for actual cutting of the defects out of the product. This is a critical part of the system since the cutting knives must handle a large volume of product with a high reliability; but, of course, under severe conditions since the cutting knives are continually moving into a cutting position and retracting.

The optical technique to sense the defect or other characteristic of the product to be removed from the associated conveyor belt should be sensitive to products varying orientations and more especially where the location of the defect on the product may vary or be located in unusual positions.

OBJECTS AND SUMMARY OF THE INVENTION

Thus, it is an object of the present invention to provide an improved defect detection system.

In accordance with the above object, there is provided a defect detection system for sensing defects in discrete pieces of similar product being carried on a conveyor belt. The vision portion of the system which senses defects includes a pair of line scan camera means, which intersect the moving belt at acute angles to effectively sense the leading and trailing edges of a piece of product. The foregoing vision module, along with a light source module and power module are are removably mounted on a cantilevered base above the moving belt. The reciprocating cutting blade units are positioned in a cross-direction above and in close proximity to the belt. They have their individual rebound characteristics compensated for by a variable driving pulse. The adjacent blade units are overlapped to ensure that the entire width of the belt is effectively covered.

BRIEF DESCRIPTION OF THE DRAWINGS

FIG. 1A and 1B are block diagrams illustrating the defect detection system of the present invention.

FIG. 7 is a side view of a blade unit of the present invention.

FIG. 8 is an end view of FIG. 7.

FIG. 9. is a diagram illustrating the placement of the blade units of FIG. 7 along a conveyor belt.

FIG. 13 is a characteristic curve illustrating values that are stored in the digital memory of a processor of the present invention.

DESCRIPTION OF PREFERRED EMBODIMENTS

Figure 1B:
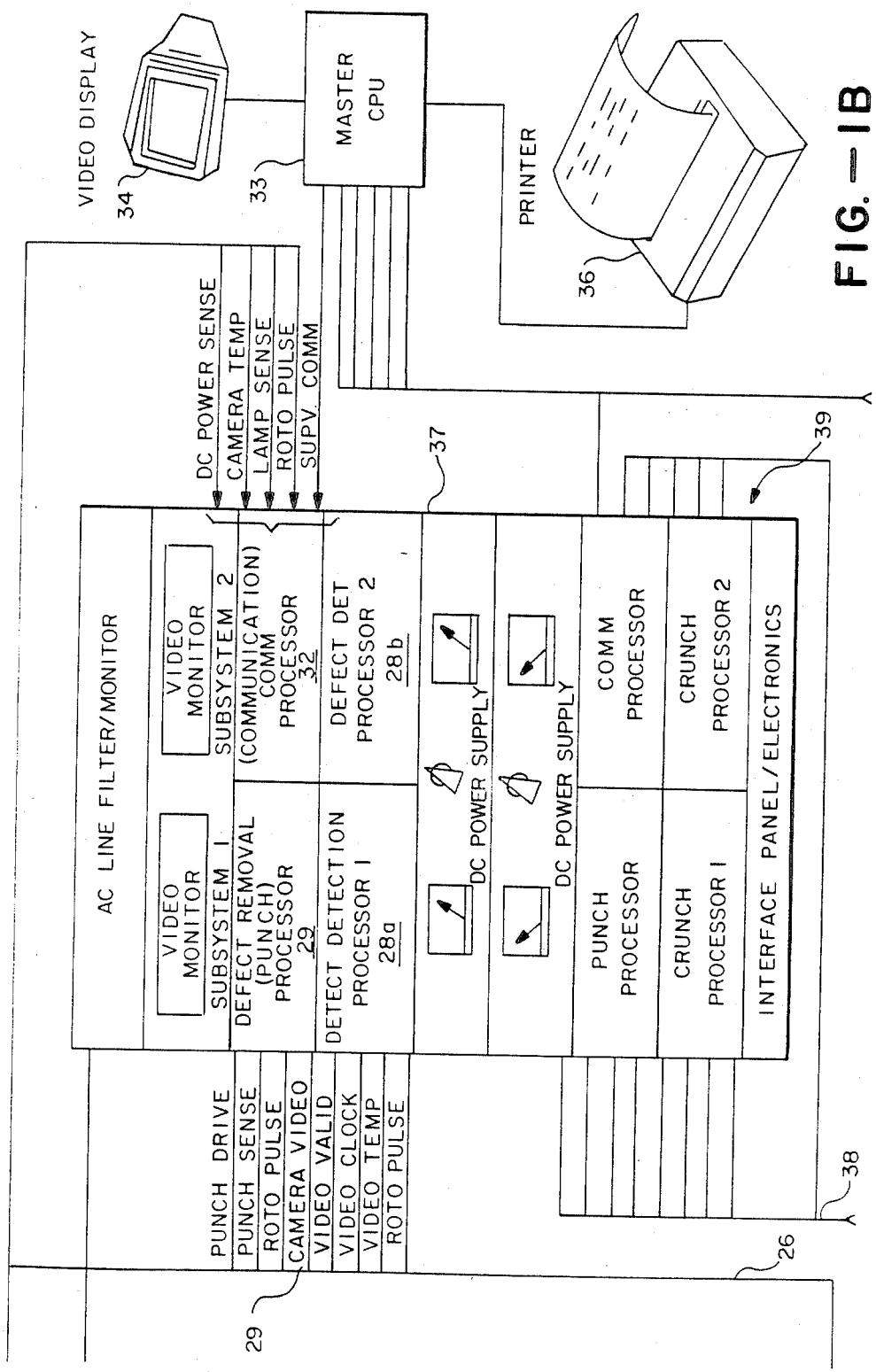

Referring to FIGS. 1A and 1B, these show a block diagram of the system of the invention. A conveyor belt 10 carries the product 11 in the direction illustrated by the arrow 12. The product can be any type of material or food or any material for which defect or size or color is desired to be detected.

However, in the present embodiment, the product 11 will be assumed to be a strip cut raw potato, which is going to be utilized for French fries, and the potato 11 may have defects, such as black spots. After being sensed by a camera module 13, the defect is cut off by a punch module 14 which drives a cutting blade 16. Thereafter, in the next stage of the process, the small defect portions may be removed by, for example, a grader which differentiates between large and small items, the small items being the ones carrying the defect and/or an air-jet operated separator which blasts the defected pieces into a receptacle allowing the good product to pass on to a conveyor belt.

The air-jet technique can also be used to eliminate all product 11 carrying defects without, in fact, cutting the defect out initially. In other words when the defect is sensed by camera module 13 and associated electronics, this information can be used merely for a separation process.

Referring in general to the system, in addition to the vision or camera module 13, there is a lamp module 17 for illuminating the product. Reflections of this illumination from the product are sensed by the camera module 13 and processed. Lamp module 17 might typically contain three high output fluorescent tubes mounted in a cross-direction to the product flow 12 driven by special high frequency ballasts to eliminate unwanted 60 and 120 Hertz components.

A power supply module 18 provides DC power to camera module 13 and punch module 14. Conveyor belt 10 is mounted on rollers 21 and 22 and is driven by a motor 23. Attached to the other end of the conveyor belt is a shaft encoder 24, which on the output line 26 produces a roto pulse which is an electronic pulse which occurs for every 1/16 of an inch of linear belt travel.

The signal is used to synchronize the camera module output 13 to track the defective product 11 after it is sensed and passes under the camera module to the punch module location 14.

In the case of the product being French fried potatoes, the camera module senses the darkness of the defect and this information is sent back to the camera video line 27 to defect detection processors 28a and 28b. The camera video signal couples with a video clock and video valid pulse to determine the synchronization of video signals out of the camera module 13. Because the width of belt 10 is 32 inches, two defect detection processors 28a and 28b are utilized, each processor manipulates data for ½ the width of the belt.

Specifically, the detection processor stores ½ inch of linear belt movement in memory and evaluates a piece of belt as it travels for defects and records its location on the belt. Where there is a defect, this information is passed to the defect removal or punch processor unit 29 which, in turn, is coupled to the punch module 14 via punch drive line 31 to cause the cutting blade 16 to operate and cut the defect. (Alternatively, this could be driving air-jets.)

Each pass of data between the defect detection processors 28 and the removal processor 29 is synchronized by the shaft encoder output 26. Thus, for every increment of the roto pulse, one instruction of data is passed between the detection and removal processors.

Thus, by the use of the roto pulse, the distance between the camera module sensing area on the belt and the actual centerline of the cutting blade 16, is known by the system.

The defect removal processor 29 as it receives data from each of the two defect detection processors 28a, 28b, loads this data into a first-in, first-out memory. The length of the memory is conceptually as long as the distance between the camera module 13 and the knife units 16. This memory is advanced each time a pulse from the shaft encoder is received. Thus, at the end of the memory, as a defect appears, it will be located under the centerline of the knife 16. And if defects exist, the removal processor will activate the knife to cut out that particular defect.

Because the defect removal and defect detection processors are substantially dedicated to their specific functions, another processor termed a communication processor 32 is provided and is used to communicate with the master CPU 33. Communication processor 32 is synchronized by the shaft encoder 24, so that it does not interrupt either the removal or the detection processors when they are performing their functions. But in between these functions, the communications processor receives data and allows the master CPU 33 to collect data on the number of defects, the size of the defect, and the various conditions which are indicated, such as temperatures in the camera module, speed of the belt, condition of the DC power sources, etc. The CPU 33 is coupled to the video display 34 and the printer 36.

As illustrated in FIG. 1B, the various processors have a DC power supply 37. In addition, other subsystems similar to that shown in FIG. 1A, may be coupled via line 38 to similar processors indicated generally at 39.

Referring to FIG. 1A, since water, air and voltage must be supplied to the various modules and the conveyor system, a supply connection unit 41 provides such inputs. Actually, since this is a food processing system in the preferred embodiment, water must be supplied to several components of the system, especially knife blade 16 for cleaning purposes.

Figure 2:
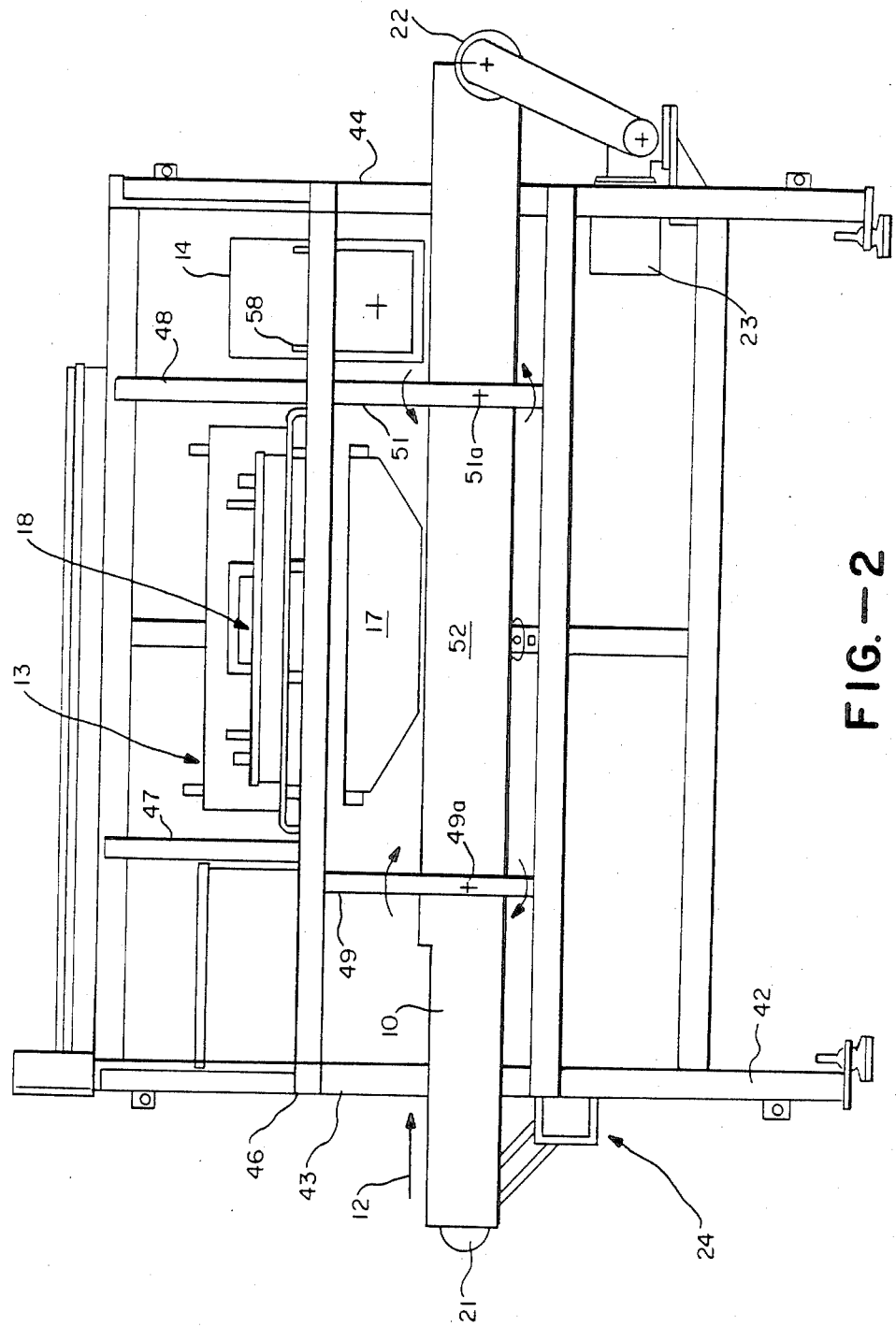
FIG. 2 is a side view illustrating the invention.

FIG. 2 illustrates the side view of the conveyor system showing the support. This includes a four-legged base 42, with a pair of vertical supports 43 and 44, extending above only one side of the conveyor belt 10.

Figure 4:
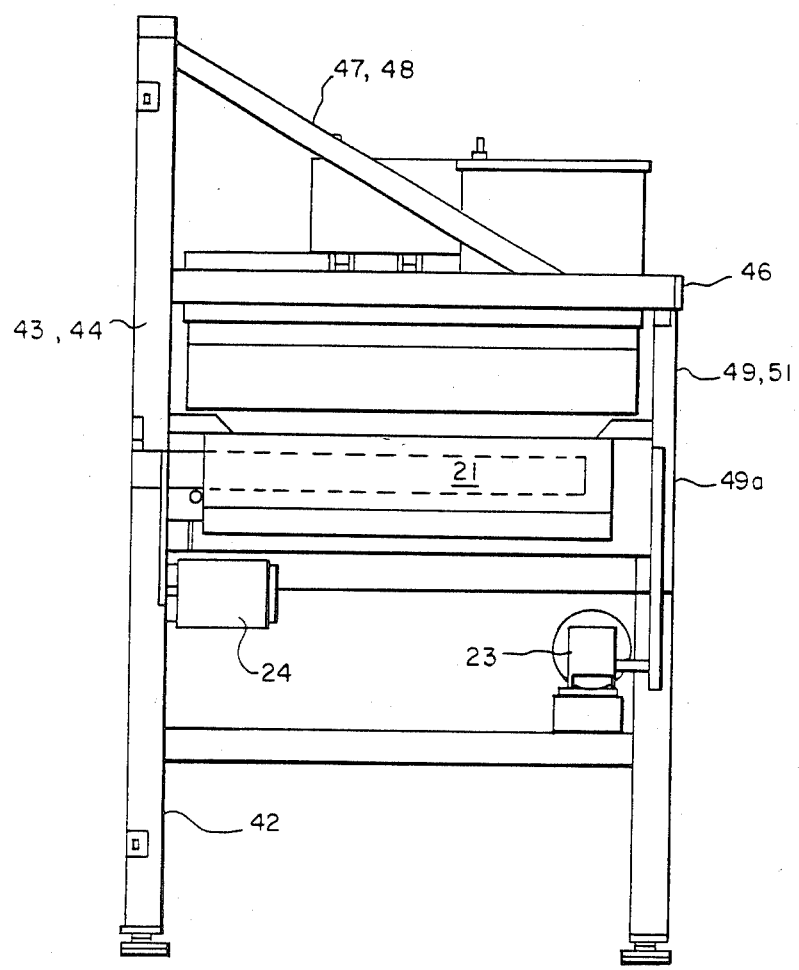
FIG. 4 is an end view of FIG. 2.

FIG. 4 is an end view and shows cantilevered from the supports 43 and 44, a mounting base 46 which is retained by the angled cross-support members 47 and 48. In order to effectively support the weight of mounting base 46 and associated components within suitable tolerances, there are provided pivotally mounted side supports 49 and 51, between the base and conveyor. These are pivoted respectively at points 49a and 51a and in conjunction with Teflon coating ends and suitable removable locks. These supports may be rotated 90° in the direction shown by the arrows in FIG. 2 to allow the conveyor belt 10 to be removed from its associated rollers 21 and 22. This is, of course, done only after the shield 52 is removed. Thus, this allows belt 10 to be a continuous uniform white polyurethane covered belt which has no joining seam which might be misinterpreted by the camera module.

In addition, such mounting allows for easy serviceability which is especially important in the case of a belt on which a cutting punch module is cutting product since inevitably the belt has a shortened lifetime. It is obvious, of course, that referring to FIG. 1A, the cutting blade 16 to effectively cut the defect carrying part of the product from the remainder of the product, must essentially cut through the entire product on the belt. With the belt moving at, for example, 180 feet per minute and with perhaps a necessary tolerance of, for example, 0.005 inches, it is difficult after a long use to avoid cuts in the belt.

And, of course, this degrades the optical reflectance quality of the belt which might impair the efficiency of the defect detection process.

Figure 3:
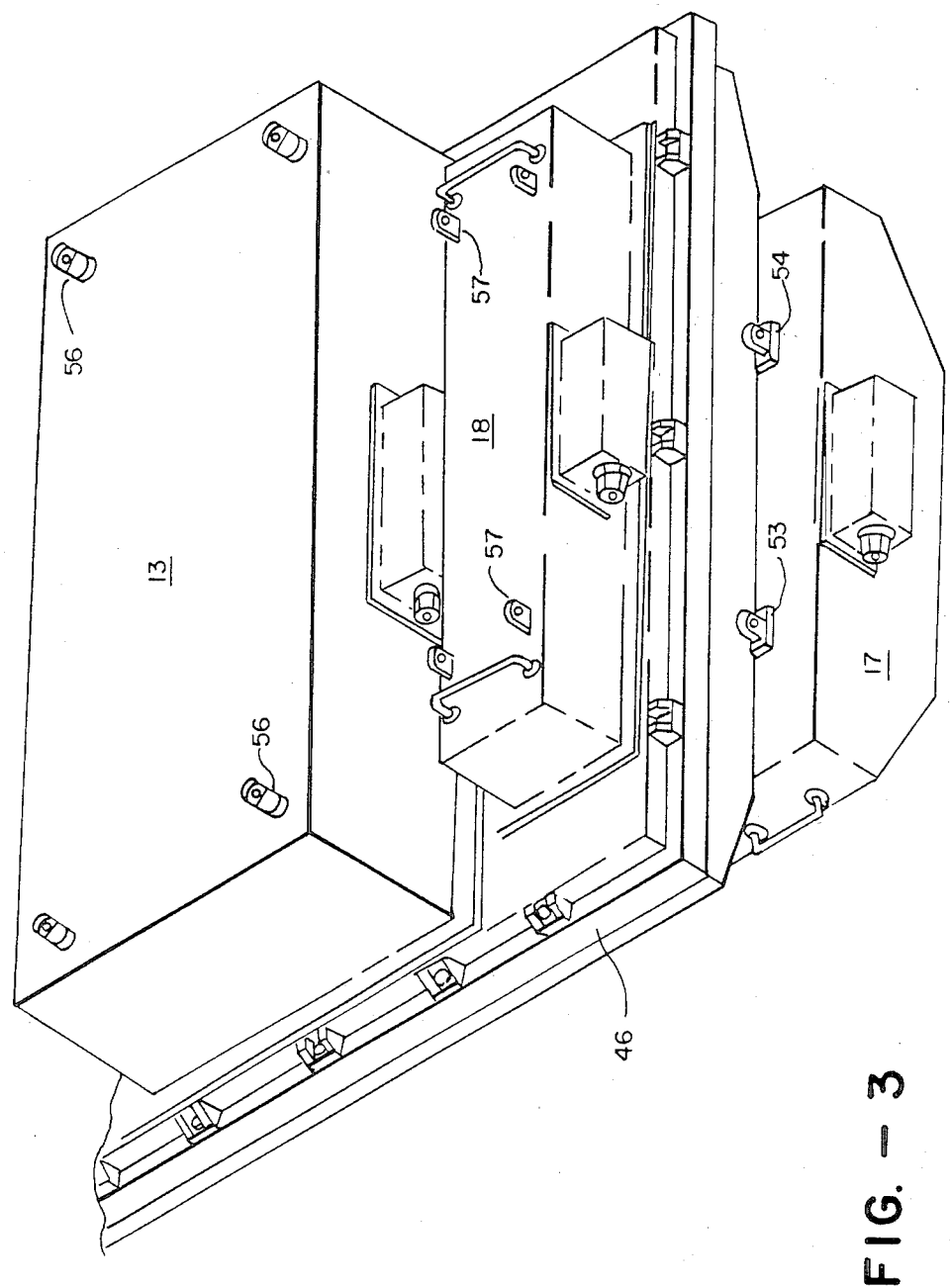
FIG. 3 is an enlarged perspective view showing a portion of FIG. 2.

As shown in FIG. 3, mounting base 46 carries on it the camera module 13 and the DC power supply module 18. Underslung from the base is the lamp module 17. These modules have quick release fittings connecting then to the base, for example, on lamp module 7, fittings 53 and 54, and also power cabling, etc., which is quick release or removable. In addition, the modules 13 and 18 include lifting hooks 56 and 57, respectively. The same is true of the punch module 14 which is also mounted on the base 46 as shown in FIG. 2, and which includes lifting hooks indicated at 58.

Thus, any module which fails can be immediately replaced to maintain the up-time of the defect detection system. And from a practical standpoint, when a system of the present invention is installed. The foregoing four modules are supplied as extras to provide for immediate onsite repair, minimizing down-time.

The location of lamp module 17 containing, for example, three fluorescent lamps, will not interfere with the line of sight of the camera module 13, as illustrated in FIG. 1A, since the line of sight or optical axes 61 and 62 of the camera module pass between the individual lamps of lamp module 17.

Figures 5, 6:
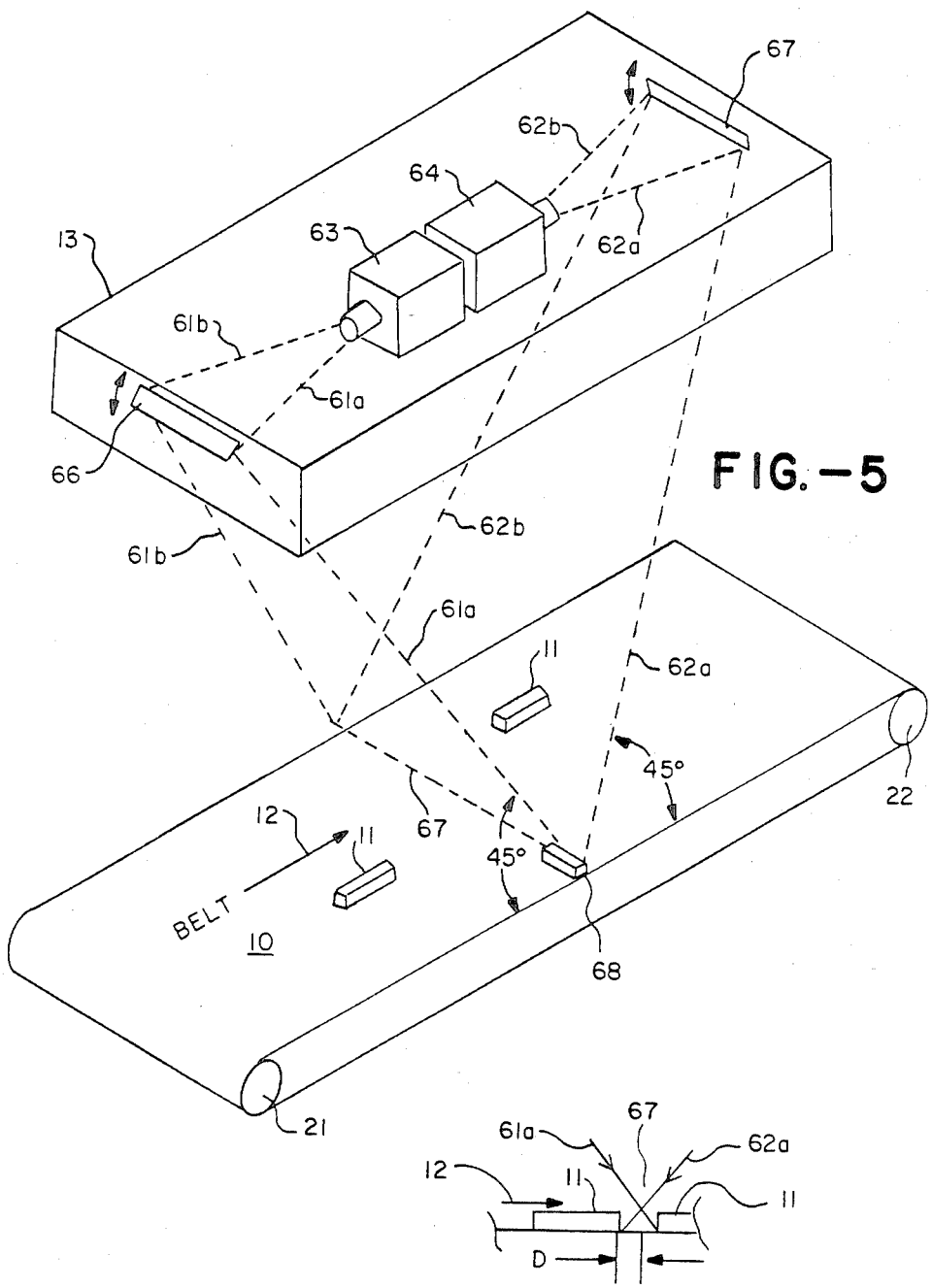
FIG. 5 is a perspective view of a portion of FIG. 1A, which has been greatly simplified.
FIG. 6 is a diagram illustrating the operation of FIG. 5.

Camera module 13 and its functioning is illustrated in greater detail in FIGS. 5 and 6. It includes a pair of line scan cameras 63 and 64, which are mounted in opposition to each other so that their line scan patterns are indicated by the line pairs in the case of camera 63 by 61a, 61b; and in the case of camera 64, by 62a, 62b. These may be conveniently redirected and adjusted by tiltable mirrors 66 and 67. The functions of these mirrors is indicated by the associated arrows. They are tilted so that the effective optical axis of the two cameras will coincide on a common line here indicated as 67, perpendicular to the direction of movement 12 of belt 10 and with each individual optical axis at an acute angle or an angle of substantially 45° as indicated. With the foregoing positioning, it is obvious that with the the cameras are being opposed to each other, and then with the associated mirror system, that their sight lines are on opposite sides of an imaginary vertical to belt 10 extending from the line 67.

Because of the acute angle and the above sight lines, the leading and trailing edges of a piece of product 11 on belt 10 as illustrated in FIG. 6, can be effectively sensed. As shown there, the axis 61a is seen at the trailing edge of product just leaving its view and the optical axis 62a is beginning to sense the leading edge of a product coming up on belt 10. The common line 67 is located at the plane of the top of the product 11. In actual practice, especially for French fried potatoes, these are actually cut to, for example, 0.290 inches as indicated and thus the line 67 will be located at that distance from belt 10.

Such location provides for a reduction in the area of uncertainty designated D in FIG. 6, which is created by the use of two cameras. For example, it is quite apparent that when the camera 64 (axis 62a) is beginning to see product 11 that the product must move the distance D before the axis 61a of camera 63 intersects that product. Thus, because of this uncertainty, the distance between a blade pair (see 16 of FIG. 1A) must be substantially equal to the uncertainty area or distance D, to accommodate the uncertainty and provide for efficient removal of any defects.

It is apparent from FIG. 6 that the location of the focus on the line 67 above the plane of the belt 10 rather than on the surface of the belt effectively reduces the area of uncertainty, D. This is especially true where the product being examined has a substantial thickness dimension; and in this case, all the dimensions, thickness, length and width are of the substantially the same order of magnitude.

Also, in the preferred embodiment of sensing strip potato, the leading and trailing edges are especially critical, since defects occur much more frequently at the potato ends than in other portions.

From a processing view, the area of uncertainty is handled by comparing the signals from the two cameras and selecting the signal with the darkest response. In other words, the defects signal.

In the drawing in FIG. 5, the block 68 is not a piece of product but merely shows the spacing of the focal line 67 above the belt 10. Note that product 11 when it is placed on belt 10 is normally located so that it is elongated in the direction of movement 12. Referring to FIG. 1A, the knife blades 16 are set up to reflect this orientation.

FIG. 7, and its side view FIG. 8, illustrate a typical cutting blade unit 16. There are four blades 69a through 69d (See FIG. 9 also for the blade orientation). The space between blade pairs, as stated, must accommodate the area of uncertainty, Alternate blades can be regarded as pairs, for example, 69a and 69c. As illustrated in both FIGS. 8 and 9, the blades are offset from one another, these degrade blades 69a and 69b. This allows each cutting blade unit, when they are positioned in a cross-direction, above and in close proximity to belt 10, to cover the entire width of the belt. This is accomplished by adjacent blade units, for example, unit 16' as illustrated in FIG. 9, having an offset of the blades in the opposite direction; this allows for convenient nesting. FIG. 9 illustrates the cutting of product 11 where the blade unit 16' is activated when the centerline 11' of the defect comes under the centerline of the cutter blade unit 16'. Thus, the offsets allow the blade units to be closely spaced to one another to provide overlapped blades in the cross-direction. Furthermore, as illustrated in FIGS. 7 and 9, three waterpipes 71a to 71c are placed between the blades 69 and include apertures in the upper portions to provide an atomized spray to continuously clean the blades. This is especially necessary in the case of processing potatoes since the starch may become a glue unless cleaned out immediately. At the same time, the location of the pipes 71 near the cutting edge in an inoperative position as illustrated in FIG. 7 (that is before the blade is actuated for cutting) will remove any product lodged between blade pairs.

Figure 10:
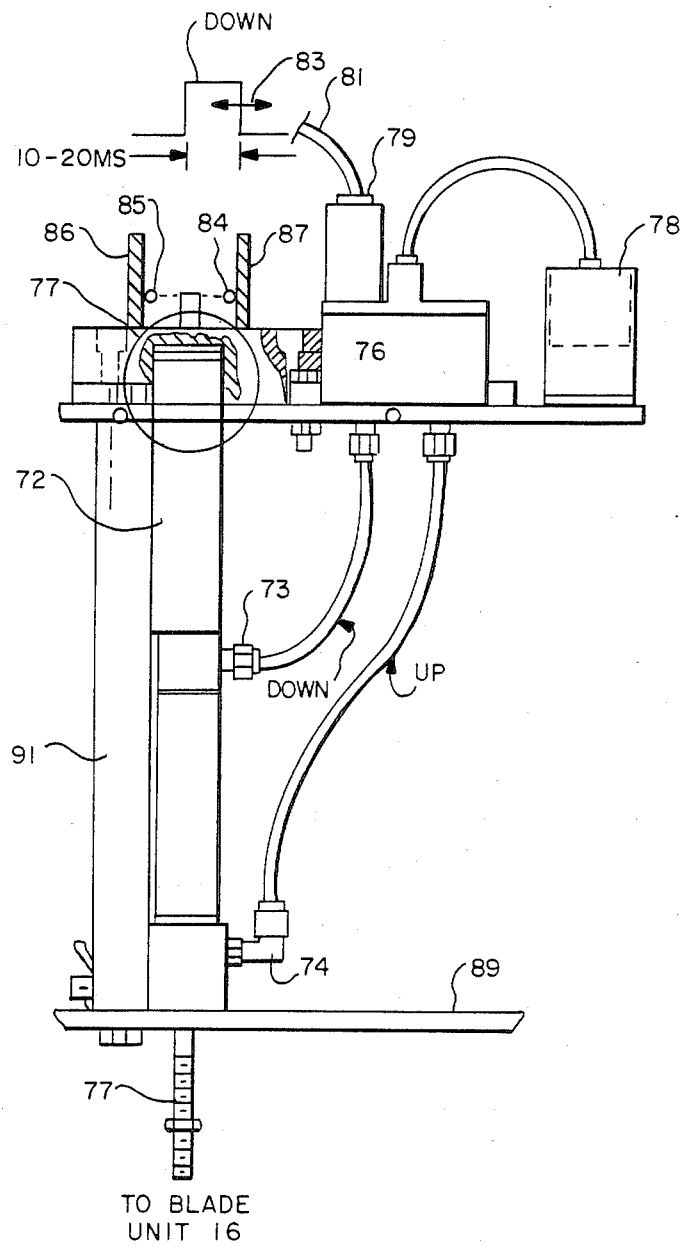
FIG. 10 is a side view of an air piston used in driving the blade units of the invention.

In order to effectively reciprocate the blade unit 16, there are provided a plurality of air piston means 72 (one for each blade unit; that is 32). FIG. 10 shows a typical air piston which has a down-port 73 and an upport 74. In other words, when air from the valve 76 is applied to port 73, the actuating rod 77 moves down (a cutting motion) and when applied to port 74 the interior cylinder is moved upward to retract blade unit 16.

Air is supplied from unit 78 to the unit 76 and an electrically driven selonoid 79 actuates the valve 76 via a pair of electrical leads 81. The pulse 82 is applied to leads 79 from the electronic circuitry shown in FIGS. 1A and 1B and specifically the punch drive line 31. It has an adjustable pulse width as shown by the double-ended arrow 83 and may vary as from 10 to 20 milliseconds.

This pulse width is adjusted to take into account the unique rebound characteristics of the specific air piston 72. Such rebound characteristics are sensed by provision of a photo cell 84 and light source 85 which are located at the top dead center (TDC) of operating shaft 77. The light source and photo cell are mounted on appropriate circuit boards 86 and 87.

Figure 11:
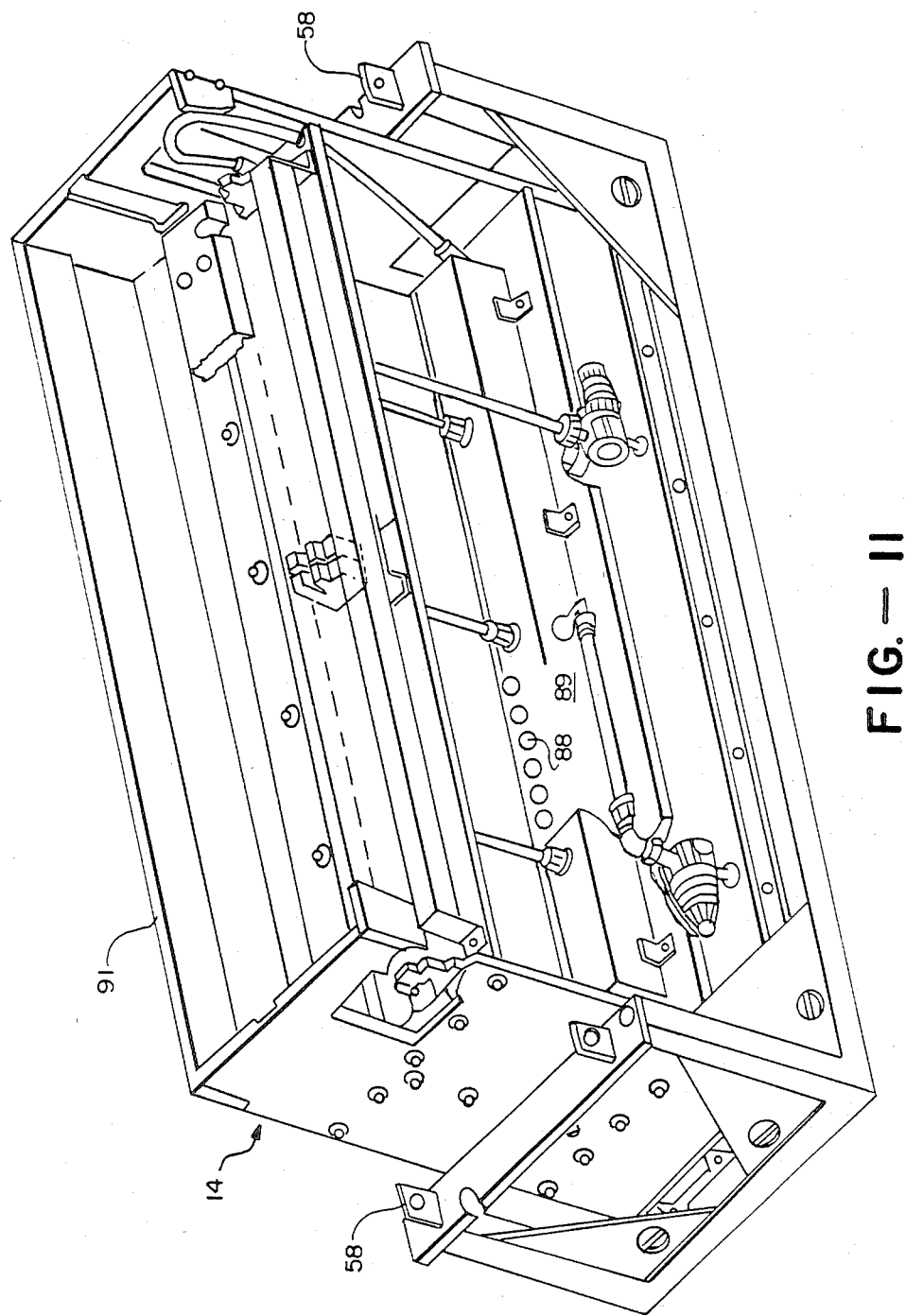
FIG. 11 is a perspective view simplified and cut-away of a module used for carrying the air piston of FIG. 10 and the blade units of FIG. 7.

FIG. 11 illustrates the module 14 which is supported mounting base 46 as best illustrated in FIG. 2. As indicated in FIG. 11, 32 of the air pistons 72 are mounted in module 14 with the activating rod 77 extending through hole 88 and the floor 89 of the module and with the cylinder 72 being mounted on the rear wall 91. (See also FIG. 10.)

Figure 12:
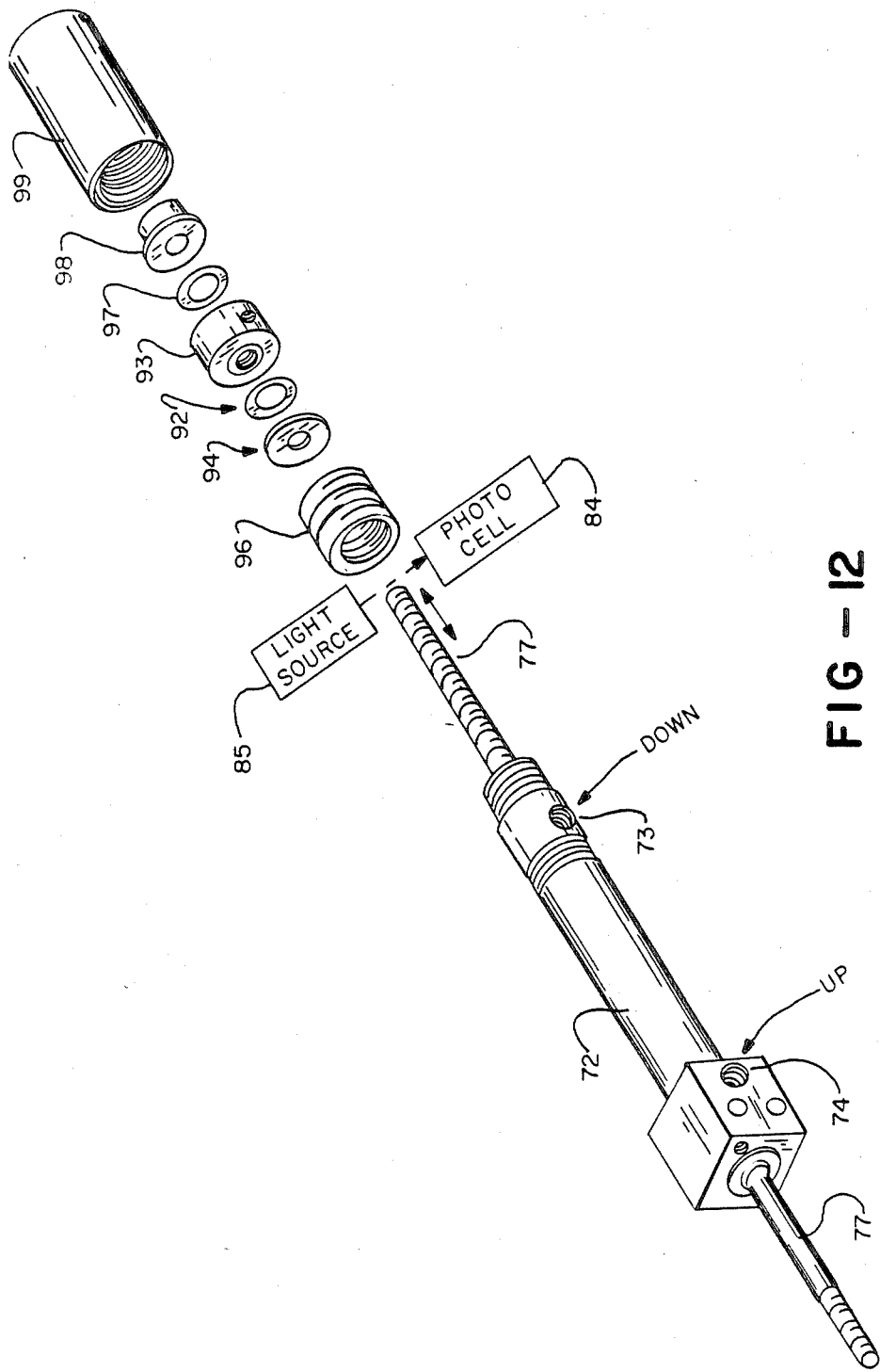
FIG. 12 is an exploded perspective view of an air piston unit illustrated in FIG. 10.

Air piston 72 and its associated elements is better illustrated in exploded format in FIG. 12. Here the down and up input ports 73, 74 are shown with an operating rod 77 which is attached to blade unit 16. Light source 85 and photo cell 84 are shown at top dead center of operating rod 77. Basically, since the air piston's body 72 is a standard off the shelf item to operate under the very fast actuating requirements of the present environment, additional stopping means external to the piston must be provided. Thus, a resilient rubber washer 92 is provided which is affixed to collar 93 which in turn is affixed by means of a locking screw to shaft 77. Washer 92 impacts against washer 94 in operation, which in turn abuts against the threaded collar 96. There is also an upper resilient washer 97 which in the upstroke 93 impacts against the fixed disc 98. All of the foregoing are covered and clamped by the threaded cylinder 99.

Thus, on the downstroke the collar 93 will impact and when air pressure is released, there will be a rebound and retraction of shaft 77. This rebound characteristic is significantly affected by the characteristics of resilient ring 92, but also the internal characteristics in the body 72 and other factors will affect this. But variation in rebound is critical enough that the pulse width 82 driving each cylinder must be uniquely adjusted. Thus, at the factory site, after the punch module 14 is constructed, the module is actuated with a pulse 82 and the photo cell output 84 sensed to obtain the TDC (top dead center) to TDC time versus pulse width as indicated in FIG. 13. When the shaft hits the bottom of its motion, this is indicated as "hit bottom." Then a further increase of the pulse width will result in a minimum in the curve, which is labeled maximum rebound velocity. Thus, this is the most efficient pulse width at which to operate this particular air piston, since it has a minimum of time. But to ensure that indeed the knife cuts through the product, the pulse width is increased slightly as indicated by the "operate here" position. This provides a minimum time of operation; the value for each of the cylinders 72 is stored in punch processor 29 as illustrated in FIG. 1B.

Furthermore, the use of an external resilient stopping means makes it easily replaced. Thus, again this ensures the system has effective uptime since one nonfunctioning blade unit seriously deteriorates the efficiency of the system.

Thus, an improved defect detection system has been provided.

What is claimed is:

1. A defect detection system for sensing defects in discrete elongated pieces of similar product being carried on a conveyor belt with the elongate axis lying in the direction of movement of the belt, each piece of product having a substantially similar and predetermined thickness dimension comprising:
   a pair of line scan camera means mounted above said conveyor belt and substantially focused on a common line perpendicular to the direction of movement of said belt, said line being located at said thickness dimension above said belt, each camera means having an optical axis which is incident with said belt at an acute angle and on opposite sides of a vertical to said belt extending from said common line, whereby the leading and trailing edges of a piece of product on said belt are effectively sensed.

2. A defect detection system as in claim 1 where said acute angle is substantially 45° whereby an area of uncertainty created by the acute angle intersection of the two cameras is minimized.

3. A system as in claim 1 where said pair of camera means include a pair of tiltable mirrors respectively associated with each camera for focusing said cameras on said common line.

4. A defect detection system as in claim 1 including cutting blade units for cutting said product to remove defects sensed by said camera means each of said units including a blade pair spaced a distance apart, relative to said direction of movement of said belt, substantially equal to the area of uncertainty created by the acute angle intersection of the optical axis of the two cameras; said area of uncertainty being determined by said acute angle and the said focus.

5. A defect detection system for sensing defects in discrete pieces of similar product being carried on a conveyor belt comprising:
   means for sensing said defects;
   a plurality of reciprocating cutting blade unit positioned in a cross-direction above and in close proximity to said belt and extending substantially across the width of said belt;
   a plurality of air-piston means, each respectively associated with a cutting blade unit for reciprocating said units to controllably cut said pieces of product having sensed said defects, each of said air-piston means having a unique rebound characteristic;
   a plurality of solenoid means for respectively actuating said air-piston means; and
   electrical means for driving said solenoid means with a pulse having a width adjusted for said rebound characteristic.

6. A defect detection system as in claim 5 where said air piston means includes an external resilient stopping means for limiting said reciprocation.

7. A defect detection system for sensing defects in discrete pieces of similar product being carried on a conveyor belt comprising:
   means for sensing said defects;
   a plurality of reciprocating cutting blade units positioned in a cross-direction above and in close proximity to said belt extending substantially across the width of said belt, each of said blade units having at least a pair of blades offset from one another in the cross-direction, said blade units being closely spaced to one another to provide overlapped blades relative to said cross direction; and
   means for controllably reciprocating said blades units to cut said pieces of product having said sensed defects.

8. A defect detection system as in claim 7 including at least one waterpipe extending through all of said blade pairs near the cutting edge of said blades for both removing product lodged between said blade pairs and for washing said blades.

* * * * *